(12) United States Patent
Bateman et al.

(10) Patent No.: US 7,152,602 B2
(45) Date of Patent: Dec. 26, 2006

(54) MASK APPARATUS

(75) Inventors: Timothy Bateman, Dyrnchurch (GB); Giles Andrew Bishop, Canterbury (GB); Stephen James Field, Canterbury (GB); Andrew James Lee, Folkestone (GB); Eric Pagan, Hythe (GB); Alan Neame Simon, Broadstairs (GB)

(73) Assignee: Smiths Group PLC, London (GB)

( * ) Notice: Subject to any disclaimer, the term of this patent is extended or adjusted under 35 U.S.C. 154(b) by 86 days.

(21) Appl. No.: 10/501,373

(22) PCT Filed: Mar. 5, 2003

(86) PCT No.: PCT/GB03/00907

§ 371 (c)(1),
(2), (4) Date: Jan. 12, 2005

(87) PCT Pub. No.: WO03/076020

PCT Pub. Date: Sep. 18, 2003

(65) Prior Publication Data

US 2005/0121030 A1  Jun. 9, 2005

(30) Foreign Application Priority Data

Mar. 8, 2002 (GB) .................................. 0205447.6

(51) Int. Cl.
*A62B 18/08* (2006.01)

(52) U.S. Cl. ............................ 128/207.11; 128/206.28; 128/206.24; 128/206.27

(58) Field of Classification Search ........... 128/206.24, 128/206.25, 206.26, 206.27, 206.28, 206.21, 128/206.29, 207.11
See application file for complete search history.

(56) References Cited

U.S. PATENT DOCUMENTS

| 2,931,356 | A |   | 4/1960  | Herman |             |
|-----------|---|---|---------|--------|-------------|
| 3,357,426 | A |   | 12/1967 | Cohen  |             |
| 4,449,526 | A | * | 5/1984  | Elam ...................... | 128/206.21 |
| 4,770,169 | A | * | 9/1988  | Schmoegner et al. .. | 128/207.13 |
| 4,794,921 | A | * | 1/1989  | Lindkvist ............... | 128/203.29 |
| 4,807,617 | A | * | 2/1989  | Nesti ..................... | 128/205.12 |
| 4,989,598 | A | * | 2/1991  | Berg et al. ............. | 128/206.23 |
| 5,143,061 | A | * | 9/1992  | Kaimer .................. | 128/206.24 |
| 5,265,595 | A |   | 11/1993 | Rudolph |            |
| 5,538,001 | A | * | 7/1996  | Bridges ................. | 128/206.24 |
| 5,752,510 | A |   | 5/1998  | Goldstein |          |
| 5,758,642 | A | * | 6/1998  | Choi ..................... | 128/206.21 |
| 6,082,360 | A | * | 7/2000  | Rudolph et al. ....... | 128/206.25 |
| 6,192,886 | B1 | * | 2/2001 | Rudolph ................ | 128/207.13 |

(Continued)

FOREIGN PATENT DOCUMENTS

WO  99/25410  5/1999

(Continued)

*Primary Examiner*—Mital Patel
(74) *Attorney, Agent, or Firm*—Louis Woo

(57) ABSTRACT

A face mask comprises a sealing collar (1) extending around the mouth with a shelf (4) extending under the nose supporting a gel insert (7) that makes sealing contact between the nostrils and a passage (6) through the shelf. A curved, rigid window (30) is a push fit in a central opening (2) of the collar (1) and has a gas inlet (33) attached with it so that the window can be removed or connected with the sealing collar as necessary. The collar (1) supported on the head by a harness (20) having two triangular portions (21) on opposite sides encircling respective ears.

15 Claims, 2 Drawing Sheets

U.S. PATENT DOCUMENTS 6,397,847 B1 * 6/2002 Scarberry et al. ...... 128/206.24
6,412,488 B1 * 7/2002 Barnett et al. ......... 128/207.13
6,467,483 B1 * 10/2002 Kopacko et al. ....... 128/207.12
6,796,308 B1 * 9/2004 Gunaratnam et al. .. 128/206.24
2002/0185134 A1 12/2002 Bishop

FOREIGN PATENT DOCUMENTS

WO 02/11804 2/2002

* cited by examiner

MASK APPARATUS

TECHNICAL FIELD

This invention relates to mask apparatus of the kind including a generally ring-shape sealing assembly adapted to be retained with the head and to seal around at least the mouth of a user, and a gas inlet for supplying gas to the apparatus.

BACKGROUND ART

Masks are used to supply air or other gas to a patient via his mouth, nose or both. Masks take many different forms but the most common comprises a semi-rigid domed shell shaped to fit around the periphery of both the nose and mouth. The shell usually has some form of softer material around its edge, which provides a seal with the skin surface. An opening in the mask includes a coupling by which the mask is connected to ventilation or anaesthesia equipment. The shell is usually retained in position by means of straps extending around the rear of the patient's head and adjustably fastened to opposite sides of the shell.

There are various problems with existing masks. One problem is that of achieving an effective seal with the contours of the face. Although it is not essential to provide a completely gas-tight seal with the skin surface, if there is not a good fit, gas escaping between the mask and skin can cause discomfort to the patient. Attempts to increase the seal by tightening the straps can increase pressure on the face, which also causes discomfort. Another problem with masks that enclose the nose is that some patients find them claustrophobic. Also, they often prevent the patient wearing spectacles. The straps used to hold the mask on the head can often be difficult to position and adjust correctly. If the mask has to be removed repeatedly to enable access to the patient's mouth it can be time-consuming to have to readjust and reposition the straps of the mask each time it is removed and replaced.

One important use of breathing masks is in CPAP (continuous positive airway pressure) or BIPAP (bidirectional positive airway pressure) ventilation for relieving sleep apnoea by keeping the airways free and open when the muscles of the respiratory tract relax during sleep. In sleep apnoea applications the mask is often worn at home. It is particularly important for such masks to be easy to use and comfortable. Where masks are used in hospitals this is often in intensive care units for patients with heart failure, pulmonary disease or other respiratory problems. CPAP is used to inflate the lungs to a higher functional capacity to allow easier and more effective oxygen transfer.

DISCLOSURE OF THE INVENTION

It is an object of the present invention to provide an alternative mask apparatus.

According to the present invention there is provided mask apparatus of the above-specified kind, characterised in that the sealing assembly has a central opening located in the region of the mouth, and a removable closure for securing with the central opening, and that the gas inlet is mounted with the closure.

The closure preferably includes a plate, which may be curved and rigid. The closure is preferably a push fit in the central opening. The sealing assembly may include a shelf adapted to extend beneath the nose of the user and the shelf may support a compliant substance adapted to seal around the nostrils. The shelf may have a passage therethrough adapted to supply gas to the user's nose. The apparatus may include a harness secured with the sealing assembly and adapted to extend around the head of the user. The harness preferably includes two triangular portions encircling respective ears of the user, both portions having a rear limb extending substantially vertically at the rear of the user's head and the rear limbs being securable with one another at the rear of the user's head. The sealing assembly may include an adhesive extending around its edge to contact the user's skin.

Mask apparatus according to the present invention will now be described, by way of example, with reference to the accompanying drawings.

BEST MODES FOR CARRYING OUT THE INVENTION

Figure 1:
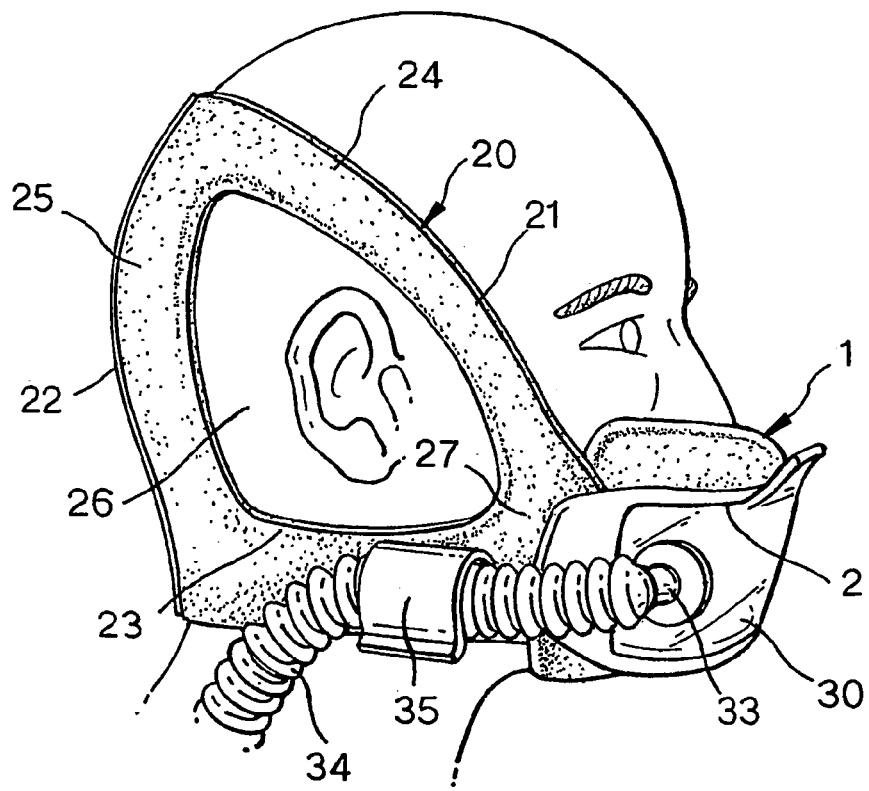
FIG. 1 is a side elevation view of the mask.
Figure 2:
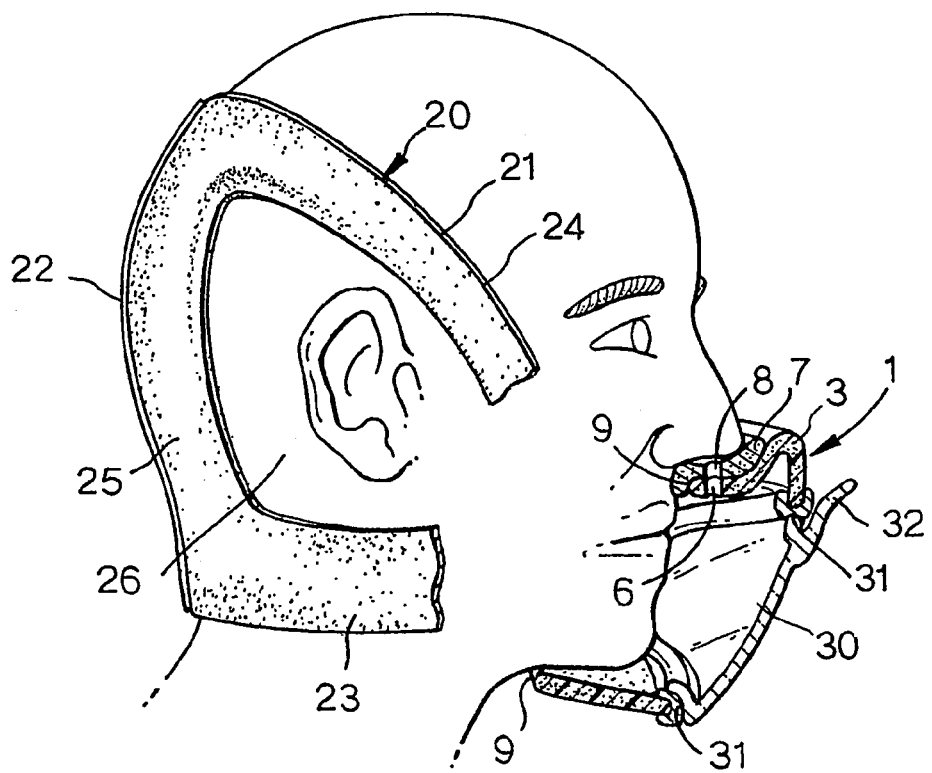
FIG. 2 is a partly cut-away side elevation view of the mask.
Figure 3:
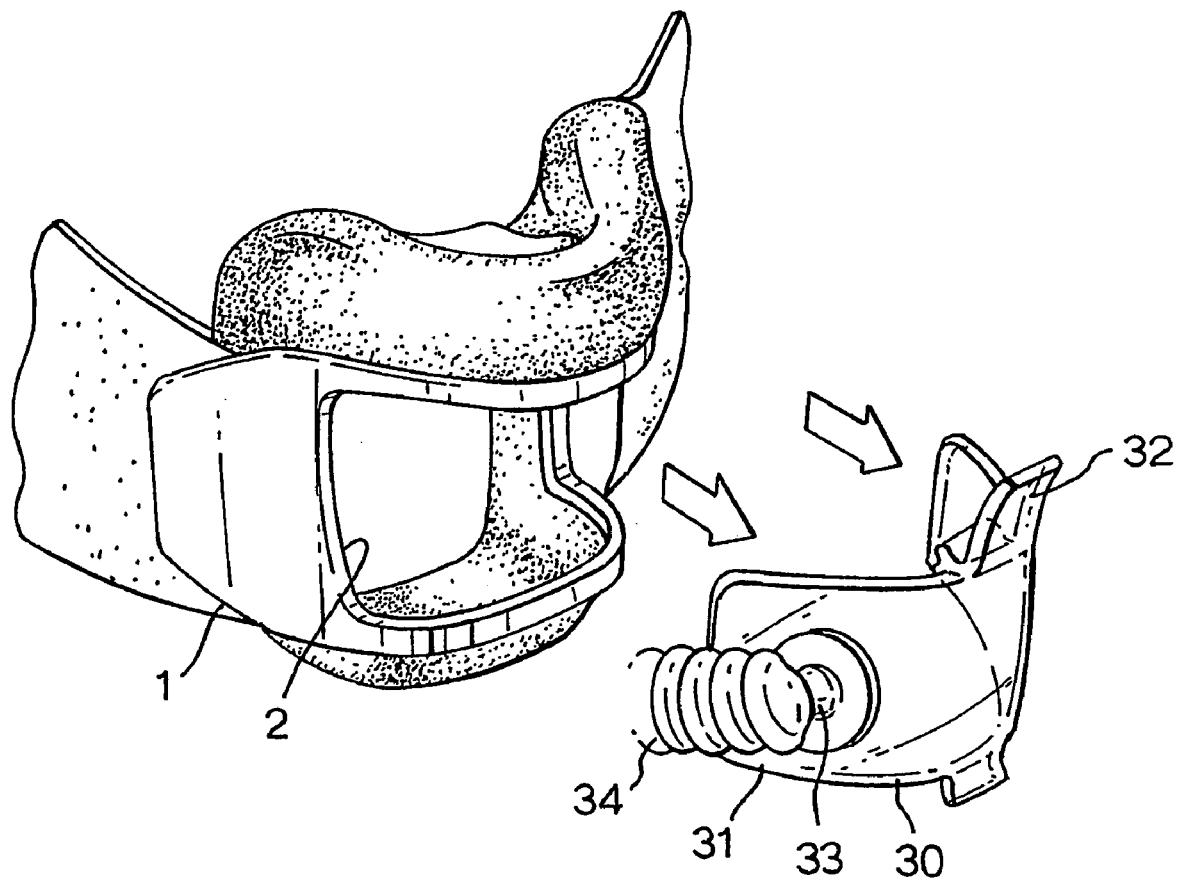
FIG. 3 is a perspective view illustrating removal of the closure means.
Figure 4:
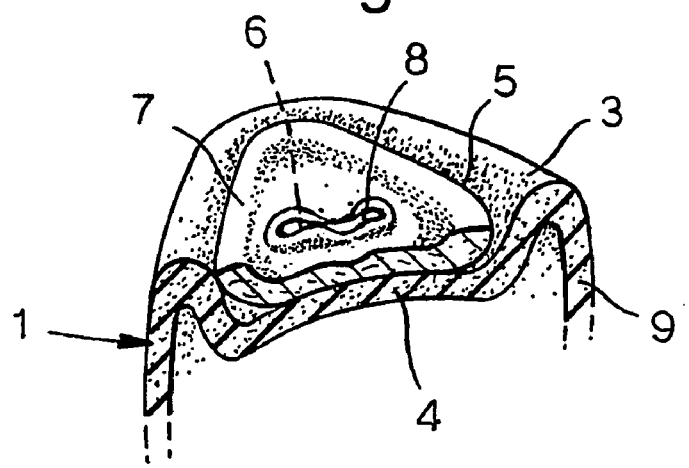
FIG. 4 is a perspective view from the rear and above of the sealing assembly.

The mask has a sealing assembly or collar 1 of a semi-rigid, impervious foamed plastics material. The collar 1 is of ring shape with a central rectangular opening 2 located in front of the user's mouth. At its upper end, the assembly 1 has a shallow part-circular wall 3 extending around a horizontal shelf 4, which forms the floor of a recess 5 in the upper end of the mask. The shelf 4 has a laterally-extending slot 6 through it positioned to align with the nostrils of the user. The recess 5 contains a wedge-shape insert 7 of a gel or similar compliant material, which also has a lateral slot 8 that aligns with the slot 6 in the shelf 4 so as to provide a gas passage to the nostrils. The gel insert 7 seals around the nostrils of the user to confine gas flow through the slots 6 and 8 to the nasal passages. The peripheral edge 9 of the collar 1 extends under the chin, up opposite sides of the mouth and across the top of the mouth between the mouth and the nose. The nature of the material of the collar 1 is such that its edge 9 conforms to the contours of the face to form an effective seal.

The seal of the collar with the patient's skin can be improved by means of an adhesive or gel strip extending around the edge 9 of the collar 1 to contact the patient's skin.

The collar 1 is attached with a harness 20 by which the mask is secured to the user's head. The harness 20 is in two portions or halves 21 that extend around the left and right sides of the user's head and that are secured together at the back of the head by engaging cooperating hook and loop fabric fasteners 22. Each half 21 of the harness 20 is formed of a single piece of flexible, breathable, elastic material of generally triangular shape with three limbs 23, 24 and 25 and a open centre 26. The forward end 27 of each half 21 of the harness is attached with opposite sides of the collar 1, two of the limbs 23 and 24 extending rearwardly from the end 27 below and above the user's ear respectively. The ears are, therefore, accommodated in the open centre 26 and encircled by the respective harness portions 21. The third limb 25 extends substantially vertically along the back of the head, joining the rear ends of the limbs 23 and 24. The third limb 25 on each half 21 of the harness supports the hook and loop fasteners 22 so that these limbs are securable with one another at the rear of the head.

Where an adhesive is used to improve the seal around the edge 9 of the collar 1, this may be sufficient to support the mask without the need for a harness.

The mask assembly is completed by a closure in the form of a cover plate or window 30 fitted in the central opening 2 of the collar 1. The window 30 is of a rigid but bendable transparent plastics material. It is generally rectangular in shape being curved substantially in a semi-circle across its width and being flat or slightly convex in a vertical direction when viewed externally of the mask. The edge 31 of the window 30 is shaped so that it is a push or click fit in the opening 2 of the collar 1, which is of a softer material. A catch tongue 32 projects forwardly and upwardly from the centre of the upper edge of the window 30. Towards one side of the window 30 there is a gas inlet port 33 connected with gas tubing 34, which extends along the side of the head and is supported by a tab fastener 35 on the harness 30.

In use, the sealing collar 1 is first positioned over the mouth with the nose received in the recess 5. The two halves 21 of the harness 20 are then passed around the side of the head and secured together at the back. In this state, the user is able to breathe through both his mouth and nose via the central opening 2 in the collar 1. When the patient needs ventilation, the window 30 with the tubing 34 attached is clipped into the opening 2. The tubing 34 is then secured with the harness 20 by means of the tab fastener 35. The transparent nature of the window 30 enables the mouth area of the patient to be viewed readily.

Access to the mouth area can be obtained by removing the window 30, simply by gripping and pulling on the catch 32. This avoids the need to remove the mask in its entirety, which is a particular advantage where a gel, adhesive or similar material is used to provide the seal or a part of the seal. The window 30 can be readily removed and replaced by the user himself where ventilation is only required intermittently.

It will be appreciated that the mask could be arranged to enclose the nose as well as the mouth.

The invention claimed is:

1. Mask apparatus including a generally ring-shape sealing assembly adapted to be retained with the head and to seal around at least the mouth of a user, a gas inlet for supplying gas to the apparatus, and a harness for retaining the sealing assembly with the head, characterized in that the sealing assembly has a central opening located in the region of the mouth and extending across the width of the mouth, and a closure in the form of a transparent window secured in the opening to extend across the width of the mouth, that the gas inlet is mounted with the window, and that the window is removable to leave the sealing assembly retained on the head by the harness such as to provide access to the region of the mouth via the opening.

2. Mask apparatus according to claim 1, characterized in that the window is curved and rigid.

3. Mask apparatus according to claim 1, characterized in that the window is a push fit in the central opening.

4. Mask apparatus according to claim 1, characterized in that the sealing assembly includes a shelf adapted to extend beneath the nose of the user.

5. Mask apparatus according to claim 4, characterized in that the shelf supports a compliant substance adapted to seal around the nostrils.

6. Mask apparatus according to claim 5, characterized in that the shelf has a passage therethrough adapted to supply gas to the user's nose.

7. Mask apparatus according to claim 4, characterized in that the shelf has a passage therethrough adapted to supply gas to the user's nose.

8. Mask apparatus according to claim 1, characterized in that the harness comprises two triangular portions encircling respective ears of the user, that both portions have a rear limb extending substantially vertically at the rear of the user's head, and that the rear limbs are securable with one another at the rear of the user's head.

9. Mask apparatus according to claim 1, characterized in that the sealing assembly includes an adhesive extending around its edge adapted to contact the user's skin.

10. Mask apparatus according to claim 1, characterized in that the gas inlet is located to one side of the window.

11. Mask apparatus including a generally ring-shape sealing assembly adapted to be retained with the head and to seal around at least the mouth of a user, and a gas inlet for supplying gas to the apparatus, characterized in that the sealing assembly includes a central opening located in the region of the mouth, a removable closure for securing with the central opening, the gas inlet being mounted with the closure, a shelf adapted to extend beneath the nose of the user, and a passage through the shelf adapted to supply gas to the user's nose.

12. Mask apparatus according to claim 11, characterized in that the shelf supports a compliant substance adapted to seal around the nostrils of the user.

13. Mask apparatus including a generally ring-shape sealing assembly adapted to be retained with the head and to seal around at least the mouth of a user, and a gas inlet for supplying gas to the apparatus, characterized in that the sealing assembly has a central opening located in the region of the mouth and extending across the width of the mouth, a removable closure in the form of a transparent window secured in the opening to extend across the width of the mouth, and a shelf adapted to extend beneath the nose of the user, and that the gas inlet is mounted with the window.

14. Mask apparatus according to claim 13, characterized in that the shelf supports a compliant substance adapted to seal around the nostrils.

15. Mask apparatus according to claim 13, characterized in that the shelf has a passage therethrough adapted to supply gas to the user's nose.

* * * * *